United States Patent [19]
Lifshey et al.

[11] Patent Number: 5,755,746
[45] Date of Patent: May 26, 1998

[54] LOCATOR METHOD AND APPARATUS

[75] Inventors: Arthur L. Lifshey, East Brunswick; Roger J. Talish, Fairfield, both of N.J.

[73] Assignee: Exogen, Inc., Piscataway, N.J.

[21] Appl. No.: 692,792

[22] Filed: Jul. 25, 1996

Related U.S. Application Data

[63] Continuation of Ser. No. 388,971, Feb. 15, 1995, abandoned.

[51] Int. Cl.⁶ .................................................. A61B 6/00
[52] U.S. Cl. ........................ 607/50; 600/439; 600/407
[58] Field of Search ..................... 607/50; 128/653.1, 128/897, DIG. 15, 660.03, 898; 378/163, 205, 206; 601/2; 604/116

[56] References Cited

U.S. PATENT DOCUMENTS

| | | |
|---|---|---|
| 4,530,360 | 7/1985 | Duarte . |
| 4,915,112 | 4/1990 | Singer .................. 128/653.1 |
| 4,981,142 | 1/1991 | Dachman . |
| 4,986,275 | 1/1991 | Ishida et al. . |
| 5,003,965 | 4/1991 | Talish et al. . |
| 5,186,162 | 2/1993 | Talish et al. . |
| 5,211,160 | 5/1993 | Talish et al. . |
| 5,259,384 | 11/1993 | Kaufman et al. ........ 128/660.01 |
| 5,285,785 | 2/1994 | Meyer . |
| 5,309,898 | 5/1994 | Kaufman et al. ............ 601/2 |
| 5,323,777 | 6/1994 | Ahonen et al. ......... 128/653.1 |
| 5,368,030 | 11/1994 | Zinreich et al. ........ 128/653.1 |
| 5,450,848 | 9/1995 | Okazaki et al. . |
| 5,456,660 | 10/1995 | Reich et al. . |
| 5,556,372 | 9/1996 | Talish et al. . |

FOREIGN PATENT DOCUMENTS

| | | | |
|---|---|---|---|
| 0456612 | 1/1975 | U.S.S.R. | ........ 378/163 |
| 1088706 | 4/1984 | U.S.S.R. | . |

*Primary Examiner*—Marvin M. Lateef
*Assistant Examiner*—Shawna J. Shaw
*Attorney, Agent, or Firm*—Dilworth & Barrese

[57] ABSTRACT

The invention relates to methods and apparatus for locating an internal injury. The apparatus includes a marker that is temporarily positionable at an external location adjacent the internal injury. The marker is formed of a material that is visible on an X-ray, magnetic resonance image, ultrasonic image, or other device for imaging the internal injury. The method includes the steps of positioning a marker at an external location adjacent an internal injury, simultaneously visualizing the marker and the internal injury, and marking an approximate external location corresponding to the internal injury. Where X-rays are used for simultaneously visualizing the marker and the internal injury, the X-ray is used to map the approximate external location corresponding to the internal injury.

23 Claims, 5 Drawing Sheets

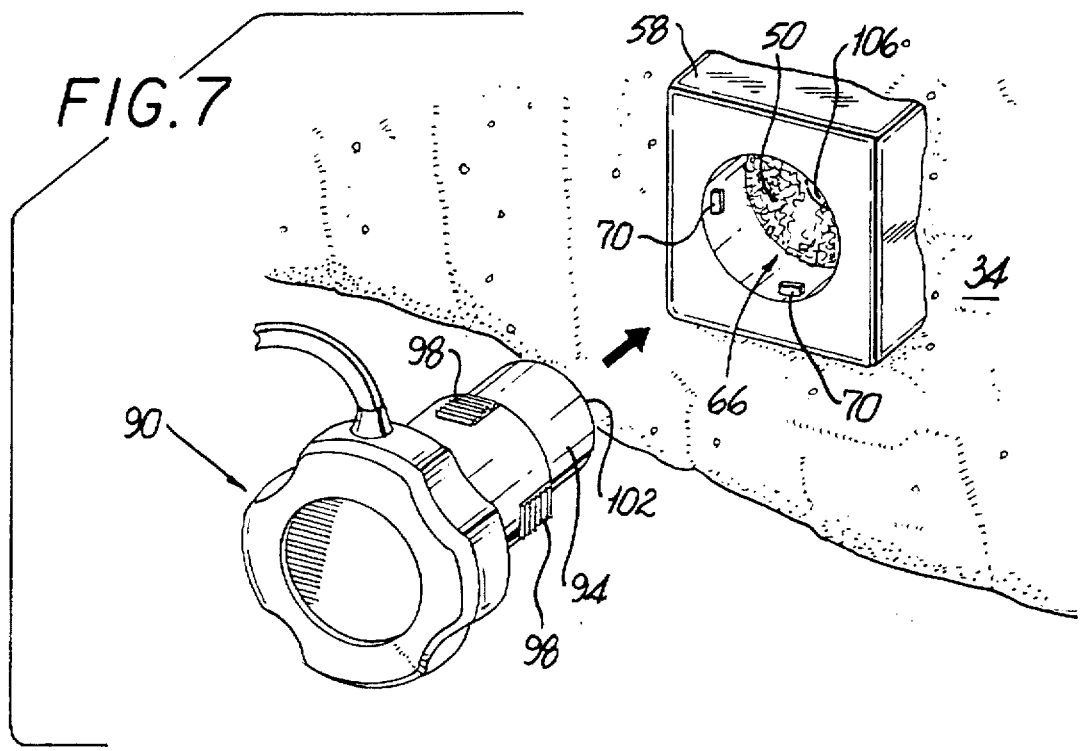
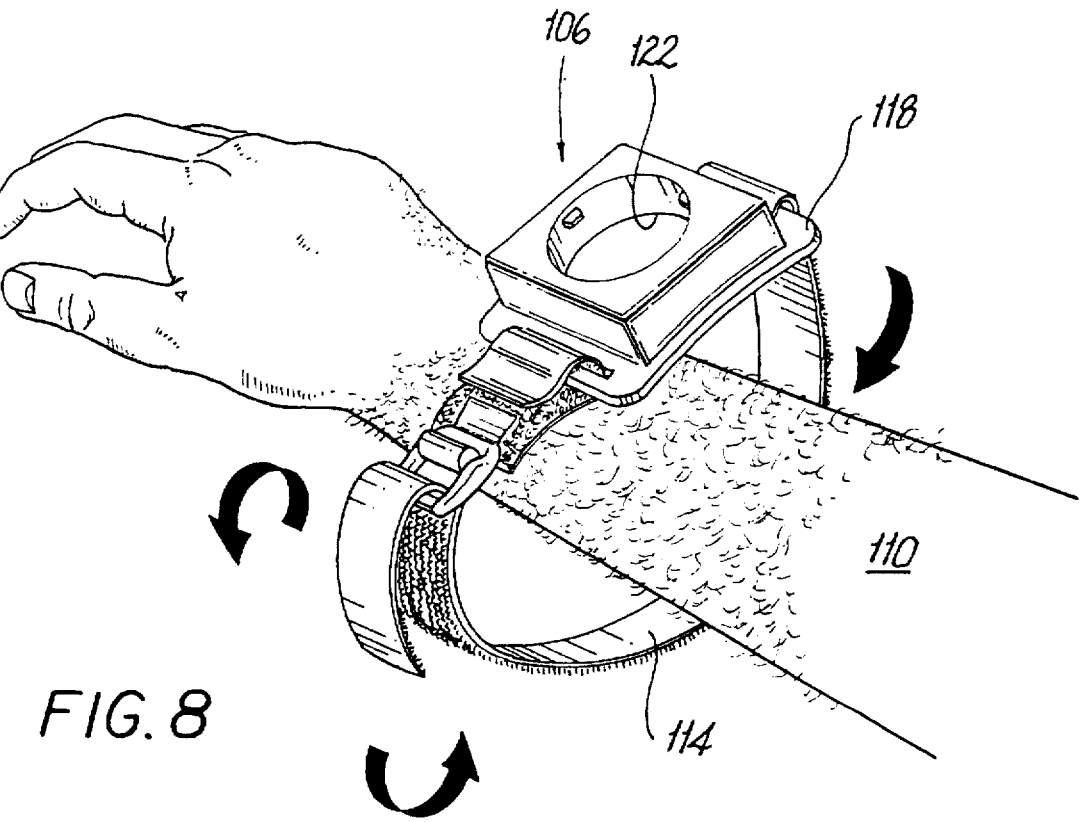

LOCATOR METHOD AND APPARATUS

This is a continuation of application Ser. No. 08/388,971 filed on Feb. 15, 1995 now abandoned.

BACKGROUND OF THE INVENTION

1. Field of the Invention

This invention relates to apparatus and methods for therapeutically treating and/or diagnosing musculoskeletal injuries by ultrasound. Ultrasonic therapy is particularly suited to hastening the healing of bone and muscle injuries—fractures, breaks, stresses and the like—but is applicable to other injuries as well.

2. Description of the Related Art

The use of ultrasound to therapeutically treat and evaluate bone injuries is known. Application of ultrasound of appropriate parameters in suitable dosages at a proper external location adjacent a bone injury accelerates natural healing with few or no adverse side effects. For patients with reduced healing capacity, such as many elderly persons, ultrasonic therapy may promote healing of bone injuries that would otherwise require prosthetic replacement or leave the patient permanently disabled.

U.S. Pat. No. 4,530,360 to Duarte ("Duarte") describes a basic therapeutic technique and apparatus for applying ultrasonic pulses from an operative surface placed on the skin at a location adjacent a bone injury. The "operative surface" of an ultrasonic delivery system, as that term is used in this application, is the exposed tangible surface of the system that transmits the ultrasonic pulses into the surroundings. For systems where the transducer surface is exposed, the operative surface is the transducer surface. Duarte gives a range of RF signals for creating the ultrasound, ultrasound power density levels, a range of duration for each ultrasonic pulse, and a range of ultrasonic pulse frequencies. The length of daily treatment is also described.

U.S. Pat. Nos. 5,003,965 and 5,186,162 both to Talish and Lifshey ("Talish '965" and "Talish '162," respectively) describe an ultrasonic delivery system where the RF generator and transducer are both part of a modular applicator unit that is placed at the skin location. The signals controlling the duration of ultrasonic pulses and the pulse repetition frequency are generated apart from the applicator unit. Talish '965 and Talish '162 also describe fixture apparatus for attaching the applicator unit so that the operative surface is adjacent the skin location. In Talish '965 and Talish '162, the skin is surrounded by a cast, while in U.S. Pat. No. 5,211,160 to Talish and Lifshey ("Talish '160") fixture apparatus is described for mounting on uncovered body parts (i.e., without a cast or other medical wrapping). Talish '160 also describes various improvements to the applicator unit.

Duarte, Talish '965, Talish '162, and Talish '160, are all incorporated into this application by reference.

While the systems described in these references, and others, disclose the underlying therapeutic method and apparatus to one skilled in the art, they do not disclose a method or apparatus for positioning the operative surface adjacent the skin for therapeutic treatment. Positioning the operative surface at the approximate external skin location of the injury optimizes the ultrasonic therapy received. If the operative surface is not correctly located, the ultrasound received at the injury may be attenuated, and the reduction in healing time is less than ideal.

It is therefore an objective of the invention to provide methods and apparatus for determining an external location corresponding to an internal injury. An external location includes a location on the skin, a cast or other medical wrapping. It is a particular objective of the invention to provide a method for delivering ultrasonic treatment at a skin location corresponding to an internal injury, in particular, a musculoskeletal injury.

SUMMARY OF THE INVENTION

To achieve these objectives, the present invention includes apparatus for determining an external location corresponding to a musculoskeletal injury comprising a marker removably positionable at an external location adjacent an injury, the marker formed at least in part of a material at least partially visible through means for visualizing the injury. Visualizing the injury may be done with X-rays, for example, and, for that case, the marker would be formed of a material visible on an X-ray, such as, for example, stainless steel.

The present invention also includes a method for determining an external location corresponding to an internal injury, comprising the steps of positioning a marker at an external location adjacent an internal injury, simultaneously visualizing the marker and the internal injury, and marking an approximate external location corresponding to the internal injury. Where X-rays are used for simultaneously visualizing the marker and the internal injury, the X-ray is used to map the approximate external location corresponding to the internal injury.

The present invention also includes a method for delivering ultrasonic treatment at a skin location corresponding to an internal injury, comprising the steps of positioning a marker at an external location adjacent an internal injury, simultaneously visualizing the marker and the internal injury, marking an approximate external location corresponding to the internal injury, and positioning an operative surface of an ultrasonic delivery system adjacent the approximate skin location corresponding to the internal injury. Where the skin is surrounded with a cast or other medical wrap, an approximate external location on the cast or medical wrapping corresponding to the internal injury is first determined. The cast or medical wrapping is then partially removed, exposing the approximate skin location corresponding to the internal injury, thereby allowing access for the operative surface to be placed adjacent the skin.

BRIEF DESCRIPTION OF THE DRAWINGS

Preferred embodiments of the invention are described below with reference to the drawings, which are described as follows:

FIG. 7 is an exploded view in perspective of a treatment module aligned with the fixture;

FIG. 8 is an exploded view in perspective of a fixture attached to a bare limb.

DETAILED DESCRIPTION OF THE PREFERRED EMBODIMENTS

Figure 1:
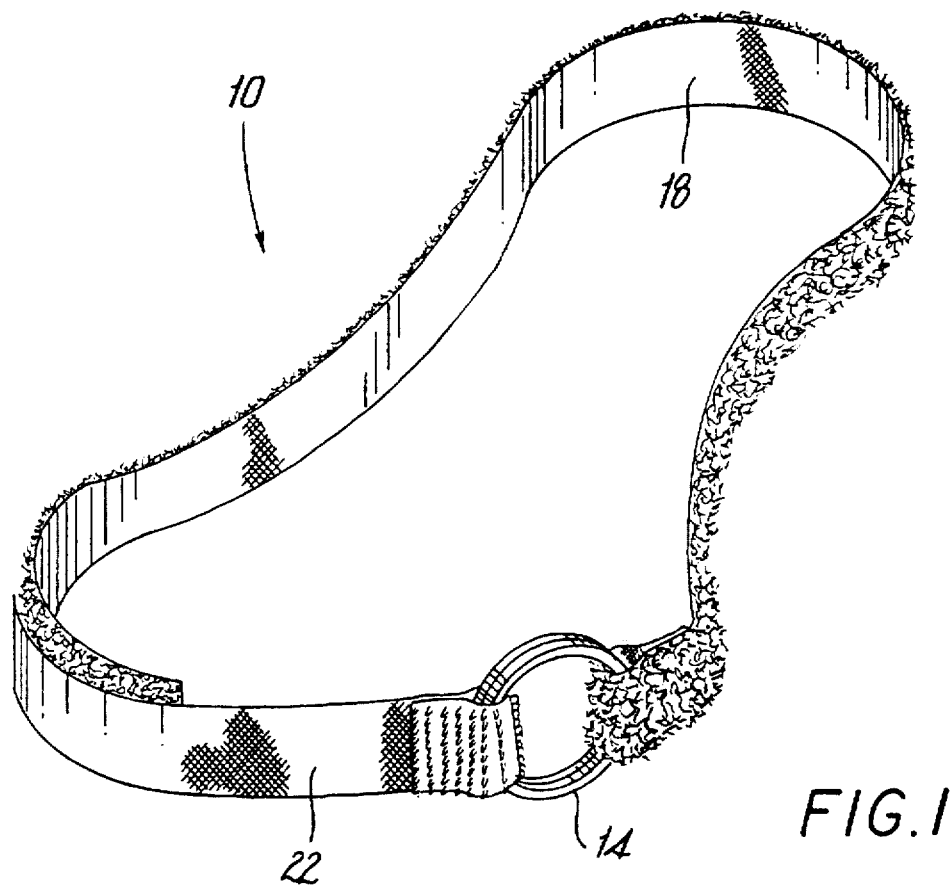
FIG. 1 is a perspective view of a locating ring and strap.

FIG. 1 shows the apparatus 10 included in the invention in the form of a locating ring 14 with a strap having two sections 18,22. The ring 14 is constructed of material that may be seen with a chosen medical visualizing system. Thus, if X-rays are used, the ring 14 is at least partially opaque to X-radiation; if infra-red radiation is used, the ring 14 is at least partially opaque to infra-red radiation; if magnetic resonance imaging is used, the ring 14 is at least partially paramagnetic.

The dimensions of the ring 14 of FIG. 1 are a function of the size of the subject, the size and location of the injury, and the visualizing system used and, should be such as to cause minimal trauma to the internal injury. For a bone fracture in an average human limb, and for visualization systems using X-rays, infrared and magnetic resonance imaging, for example, the diameter of the ring may nominally be 1.5 inches, the ring may be a rigid torus of metallic material of cross-sectional diameter nominally 0.2 inches. If the visualization system uses ultrasound in the above circumstances, the ring is substantially flexible and planar, so that it may contour to a surface it is placed adjacent to, thereby allowing the transducer to be moved across the surface and the ring.

The strap of FIG. 1 has two sections 18,22, each section fastened to the ring 14. The two sections 18,22 have hook and loop type fastening assembly so that they may be fastened together. Other fastening and adjustment means may be substituted.

FIGS. 2 through 7 demonstrate one sequence of the invention in method. The following description presumes that the medical visualizing system is an X-ray, but it is easily adaptable to other such systems, including those referred to above.

Figure 2:
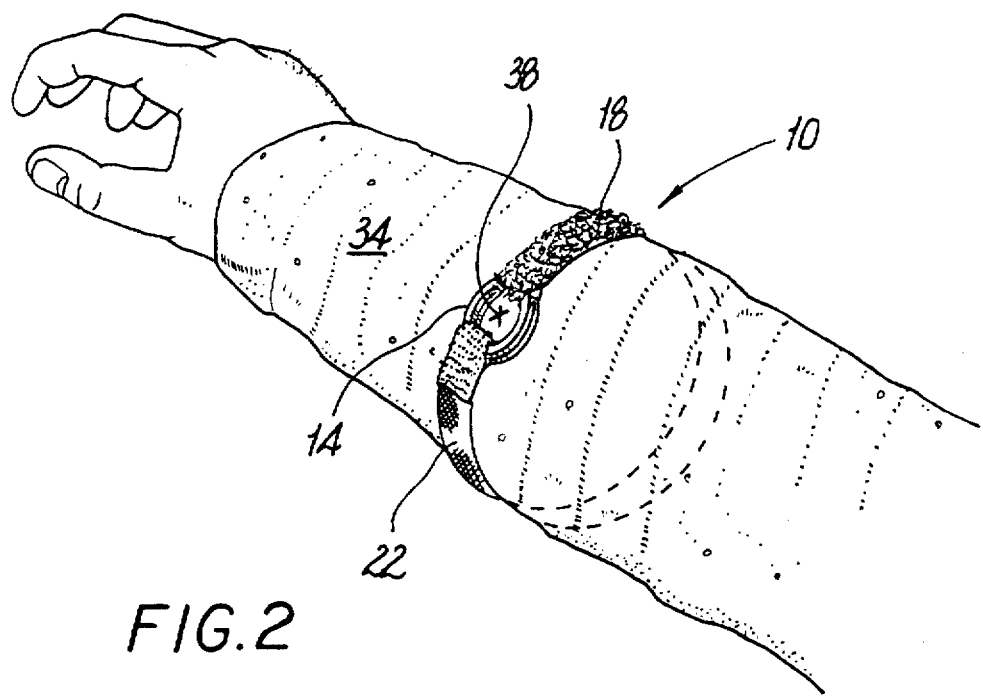
FIG. 2 is a perspective view of a locating ring and strap mounted adjacent a limb with a cast surrounding it.

FIG. 2 shows the apparatus 10 of FIG. 1 strapped to a limb with a cast 34. The locator ring 14 is initially positioned on the cast 34 at a location corresponding to the bone fracture. This initial position is a preliminary approximation of the external location of the bone fracture, and may be based on previously taken X-rays, or the physician or patient's recall of the point of injury on the surface.

An external X-ray of the fractured region is taken to include the locating ring 14. Although the initial position of the locating ring 14 with respect to the internal injury is a preliminary approximation, in many instances the initial placement will be sufficiently accurate so that the X-ray will depict the internal injury framed by the ring 14.

The X-ray shows the position of the bone fracture relative to the locating ring 14. The X-ray is used as a guide to locate and mark 38 the corresponding point on the cast relative to the actual locating ring 14. The mark 38 gives an approximate external location on the cast of the bone fracture. If greater accuracy is required, the ring 14 may be centered about the mark 38, another X-ray is taken, and a new mark (not shown) is made on the cast based on the location of the bone fracture relative to the ring on the X-ray. Successive iterations of repositioning the locating ring 14 and X-raying the site will yield even greater accuracy.

Figure 3:
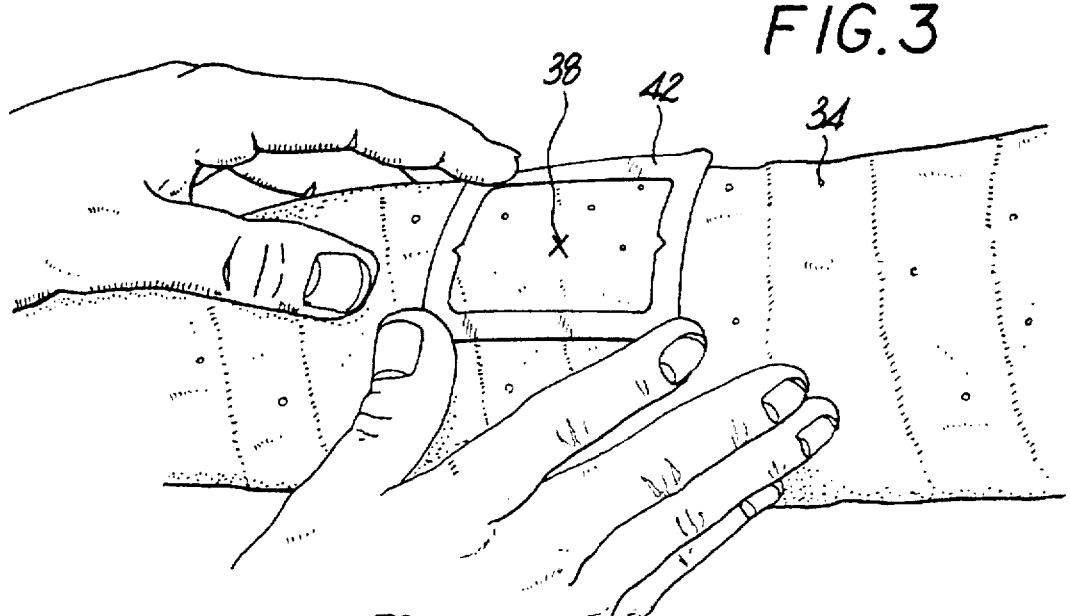
FIG. 3 is a perspective view of a template centrally located over a mark on the cast.
Figure 4:
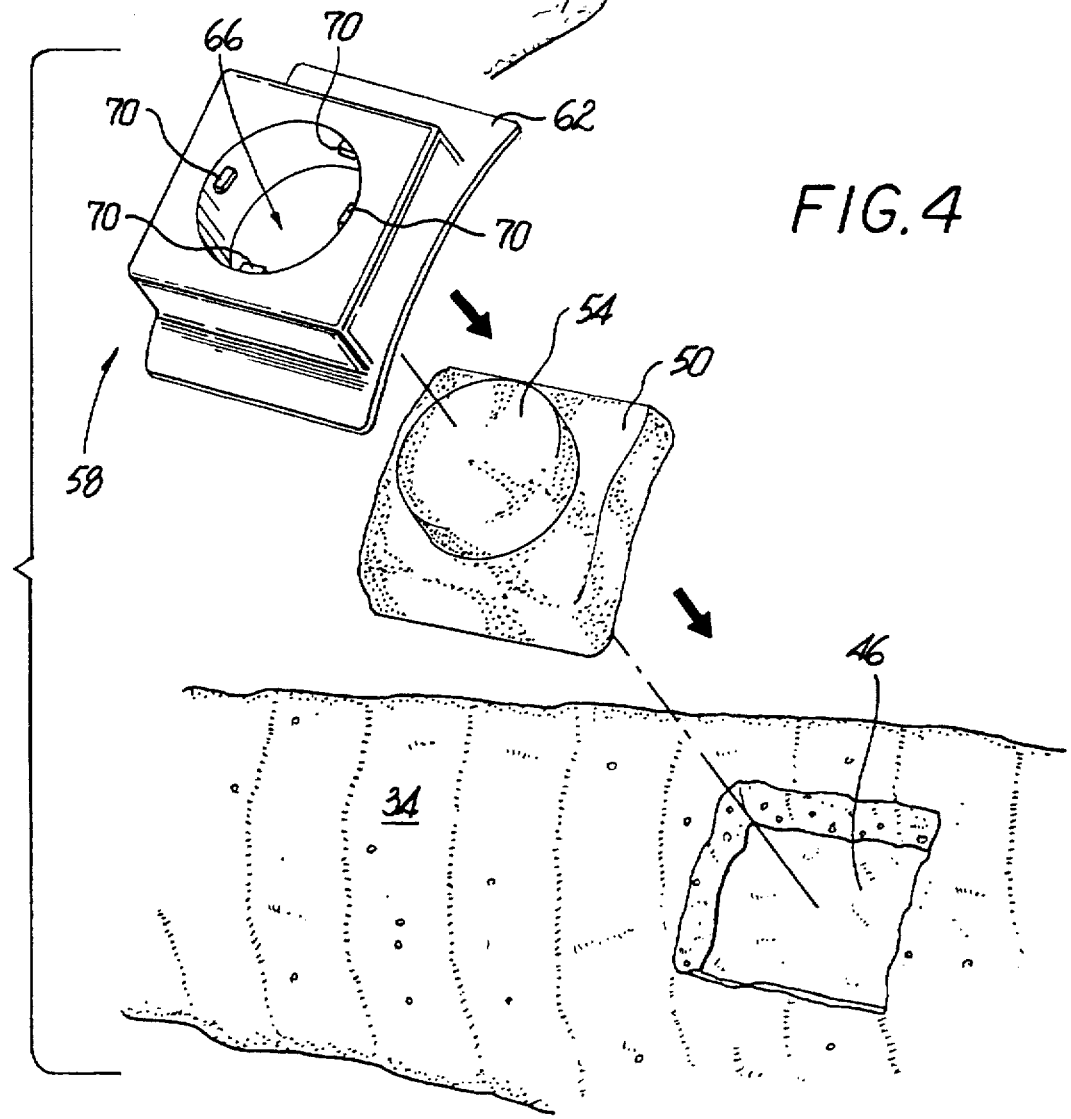
FIG. 4 is an exploded view in perspective of the cast with a removed section and a fixture for retaining and aligning an ultrasonic treatment module.

As shown in FIG. 3, a rectangular template 42 is pressed against the cast 34 and centered on the mark 38 of the external location on the cast 34 of the bone fracture. The outline of the inner edges of the template opening is traced on the cast 34, and the traced portion of the cast is removed so that the opening in the cast 46 exposes the skin, as shown in FIG. 4. As also shown in FIG. 4, the removed portion of the cast receives a felt pad 50 of approximately the same thickness of the cast. The pad 50 also has a cylindrical bore that receives a cylindrical felt pad 54. The template 42, and consequently the opening in the cast 46, is smaller than the flange 62 of a fixture 58 for retaining and aligning an ultrasonic treatment module, so that the flange 62 engages the cast surface surrounding the opening 46 when it is placed over the opening 46. The fixture 58 also has a circular aperture 66 and bayonet locking lugs 70. Aperture 66 has substantially the same diameter as the cylindrical felt pad 54.

Figure 5:
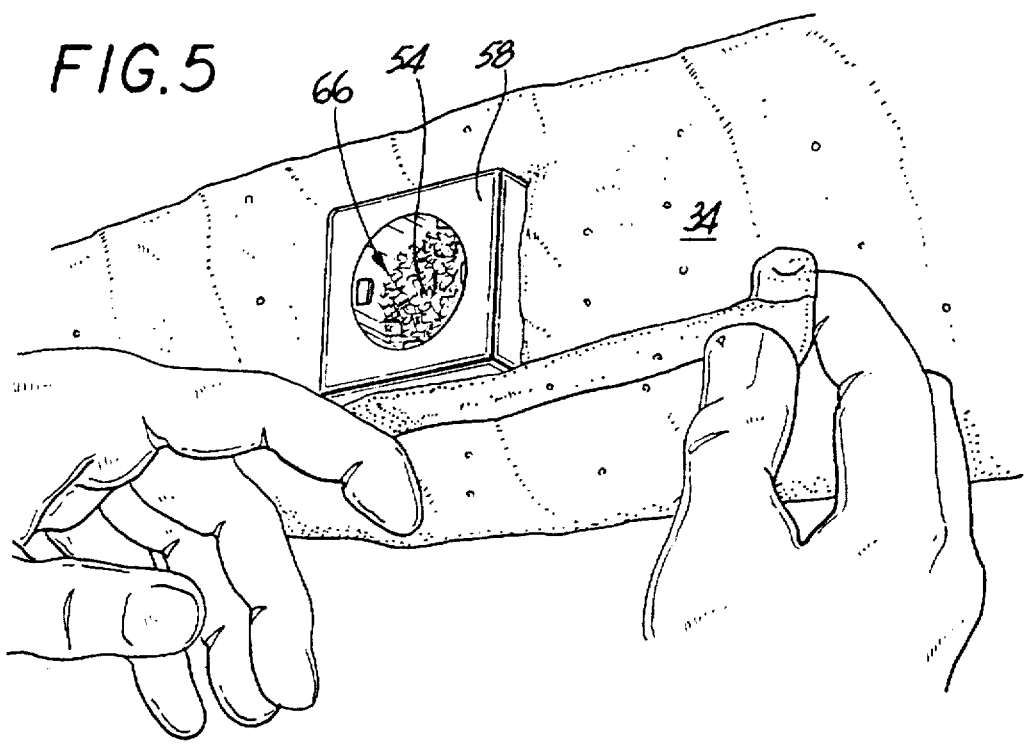
FIG. 5 is a perspective view of the fixture being secured to the cast at the removed section.

FIG. 5 shows the fixture 58 positioned over the opening of the cast 34 and the felt pad 50 so that the aperture 66 and the cylindrical felt pad 54 are coaxially aligned. The fixture 58 partially compresses the felt pad 50 (seen in FIG. 4) against the skin as its flange 62 (seen in FIG. 4) engages the cast 34, thereby approximating the pressure of the removed portion of the cast where the felt pad engages the skin.

Figure 6:
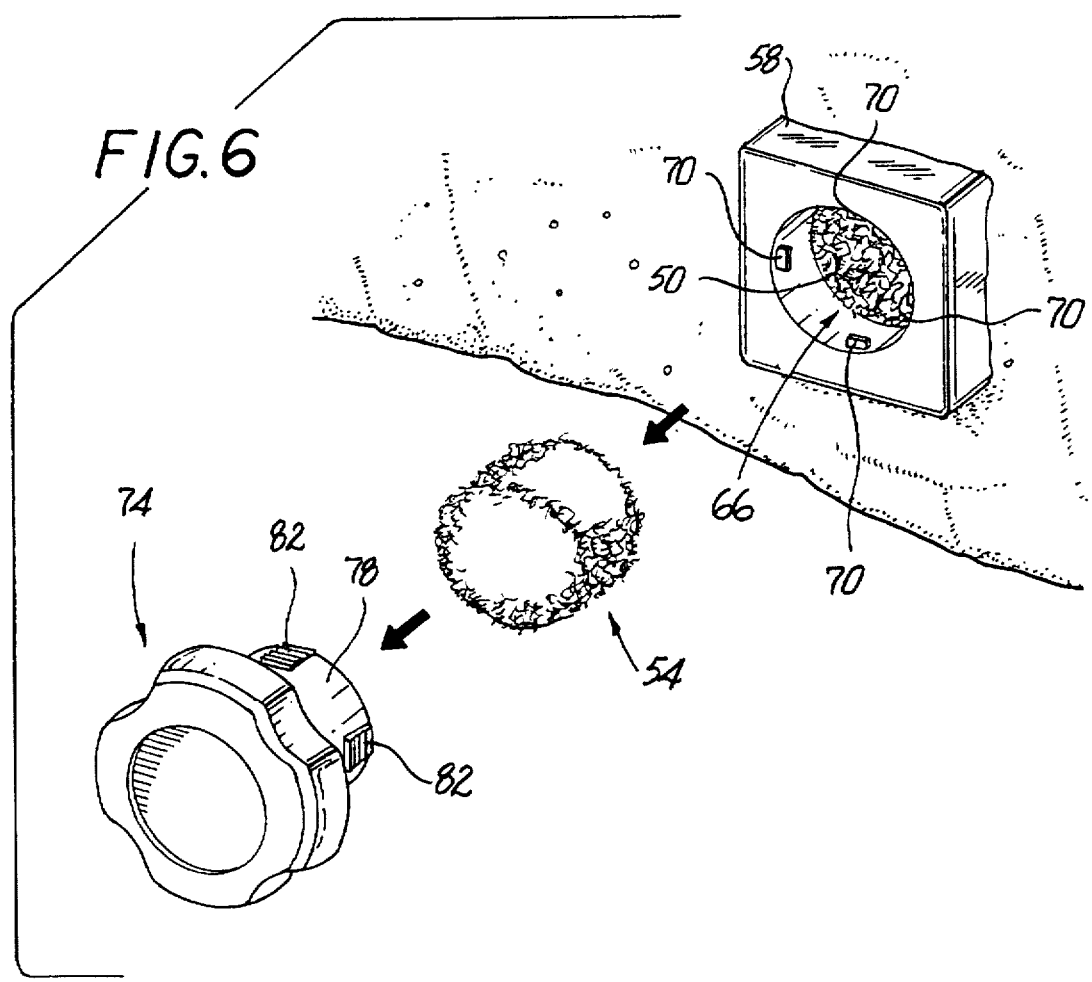
FIG. 6 is a perspective of the cast, the fixture and a cap for the fixture.

FIG. 6 shows a cap system for the fixture 58 for use when the daily ultrasonic treatment is finished. A cap 74 has a cylindrical portion 78 that extends into the aperture 66 of the fixture 58. The cap 74 has slotted lugs 82 on the cylinder 78 that engage the bayonet lugs 70 in the fixture 58. The cylindrical felt pad 54 is positioned in the aperture 66 and the cylindrical portion 78 is inserted into the aperture 66 with the slotted lugs 82 offset from the bayonet lugs 70. The slotted lugs 82 are configured to allow the cap 74 to be maintained at a predetermined depth relative to the fixture 58. This allows for a correct pressure on felt pad 54. The cap 74 is pressed against the felt pad 54 until the pressure exerted by the cap 74 and cylindrical felt pad 54 against the skin approximates the pressure of the cast 34. This pad 54 creates a pressure on the skin surface when the fixture is closed by cap 74 in order to inhibit window edemas at that location. (The felt pad 54 may also be comprised of substantially planar circular layers that may be removed one layer at a time in order to adjust the thickness of the felt pad and the resulting pressure against the skin.) The cap 74 is then rotated so that its slotted lugs 82 engage the bayonet lugs 70.

FIG. 7 is an exploded view in perspective of the treatment module 90 and the fixture 58. The module projection 94 has slotted lugs 98 that engage the bayonet lugs 70 disposed adjacent the outer surface of the fixture 58. With the cap 74 and cylindrical felt pad 54 (shown in FIG. 6) removed, the module projection 94 fits into the aperture 66 of the fixture 58 (and the bore of the felt pad 50), and is inserted with the slotted lugs 98 offset from the bayonet lugs 70. The operative surface 102 of the module 90 is pressed adjacent the skin 106 and the module 90 is then rotated so that its slotted lugs 98 engage the bayonet lugs 70. Slotted lugs 98 are configured to allow the treatment module 90 to be maintained at a predetermined depth relative to the fixture 58. The ultrasonic treatment then commences.

The operative surface 102 is normally pre-coated with a coupling gel before it is inserted in the fixture 58 and engages the skin 106. The gel may be contained adjacent the operative surface 102 using a gel sack, gel bladder or like container.

FIG. 8 shows another variation of the invention, with a fixture 106 attached to a bare limb 110 by means of a strap 114. The radial flange 118 of the fixture 106 engages the skin, and a foam backing 122 is compressed, when the strap 114 is fastened and tightened.

The fixture 106 is positioned to the approximate skin location of the bone injury using a method analogous to that described above: that is, a locator ring is attached directly to the limb at an external skin location in the vicinity of the injury, an X-ray is taken of the injury and the ring, and an approximate skin location of the bone injury is marked on the skin using the relative positions of the injury and ring on the X-ray as a guide.

A non-permanent mark, using a temporary tatoo or magic marker, for example, may be used on the approximate skin location so that the fixture 106 may be removed when there is no treatment and accurately re-attached for the ultrasonic therapy.

Figure 9:
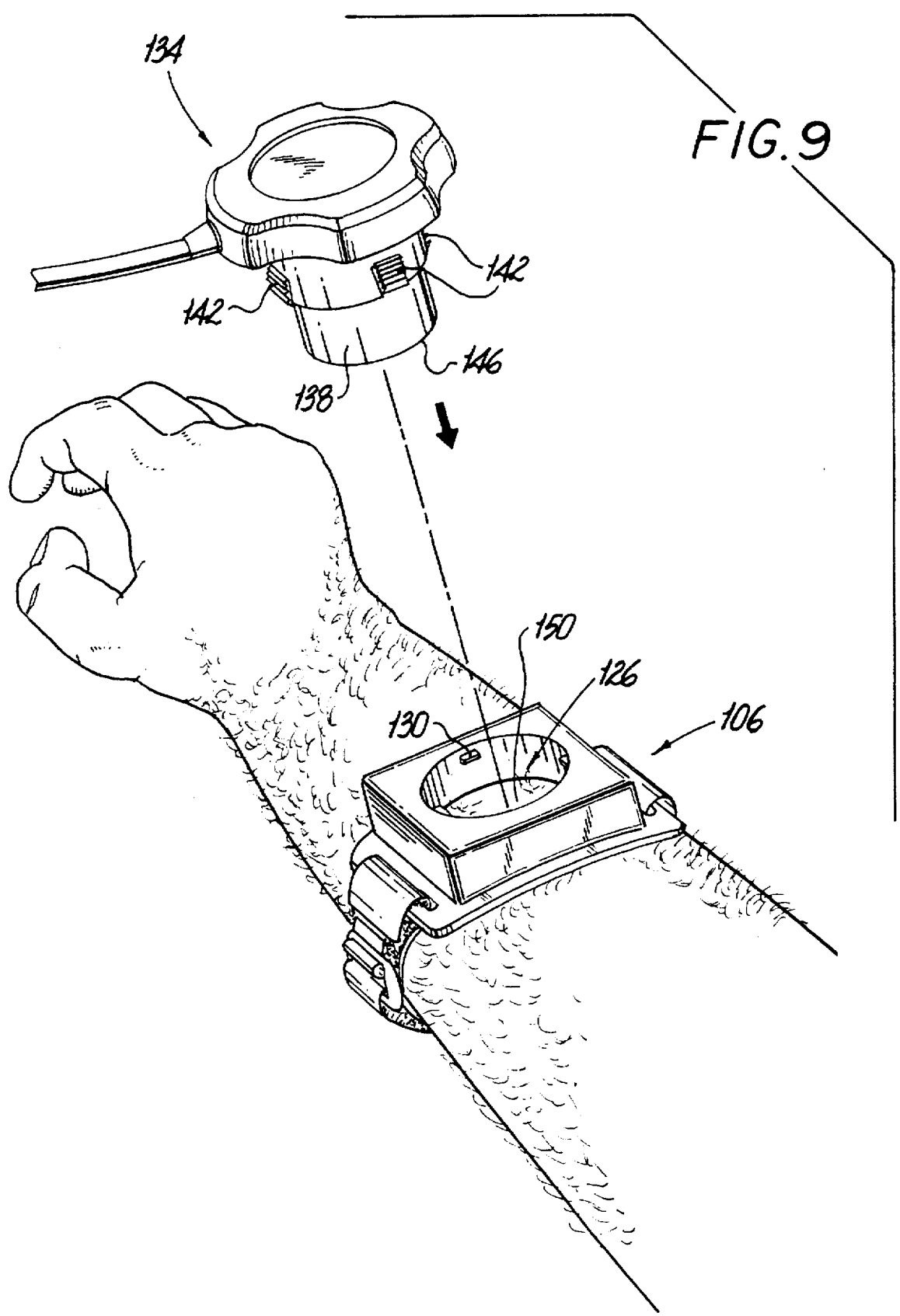
FIG. 9 is an exploded view in perspective of a fixture and a treatment module attached to a bare limb.

FIG. 9 is an exploded view in perspective of the treatment module 134 and the fixture 106 in use on a bare limb 110. As above, the module projection 138 fits into the aperture 126 of the fixture 106. Placement of the module 134 for ultrasonic therapy proceeds as above: the module projection 138 is inserted with the slotted lugs 142 offset from the bayonet lugs 130. The end of the module projection 138 housing the operative surface 146 is pressed against the skin 150 (again, the operative surface is normally pre-coated with a coupling gel) and the module 134 is then rotated so that its slotted lugs 142 engage the bayonet lugs 130. The ultrasonic treatment then commences.

It will be understood that various modifications can be made to the various embodiments of the present invention herein disclosed without departing from its spirit and scope. For example, various sizes and shapes of the locator ring are contemplated, as well as various types of construction materials. Also, various modifications may be made in the configuration of the parts. For example, the locator ring may be positioned using an elastic band or even adhesive tape. Similarly, various modifications may be made to the above-described sequence of the invention in method without departing from its spirit and scope. For example, the flange of the fixture itself may be used to mark the opening on the cast, instead of using a template. Therefore the above description should not be construed as limiting the invention but merely as presenting preferred embodiments of the invention. Those skilled in the art will envision other modifications within the scope and spirit of the present invention as defined by the claims presented below.

What is claimed is:

1. Apparatus for determining an external location corresponding to a musculoskeletal injury, comprising:
    an annular ring defining a marker which is removably positionable at an external site adjacent a musculoskeletal injury, the ring formed at least in part of a material at least partially visible through means for visualizing the musculoskeletal injury and being dimensioned to cause minimal trauma to the musculoskeletal injury; and
    an elongated strap for securing the annular ring at the external site, the strap having opposed end portions respectively connected to diametrically opposed arcuate sections of the annular ring so that a central spacial region circumscribed by the ring is substantially unobstructed by the strap.

2. Apparatus as in claim 1, wherein the strap includes adjustment means for selectively varying the operative length of the strap.

3. Apparatus as in claim 2, wherein the adjustment means is a hook and loop type fastening assembly.

4. Apparatus as in claim 1, wherein the ring is formed from a metallic material.

5. Apparatus as in claim 1, wherein the ring is formed from a material which is at least partially opaque to X-radiation.

6. Apparatus as in claim 1, wherein the ring is formed from a material which is at least partially opaque to infrared radiation.

7. Apparatus as in claim 1, wherein the ring is formed from a material which is at least partially paramagnetic.

8. Method for determining an external location corresponding to a muscloskeletal injury, comprising the steps of:
    a) positioning a marker at an external location adjacent a musculoskeletal injury;
    b) simultaneously visualizing the marker and the musculoskeletal injury;
    c) marking with indicia an approximate external location corresponding to the musculoskeletal injury;
    d) repositioning the marker at the indicia marking the approximate external location corresponding to the musculoskeletal injury; and
    e) repeating steps (b) and (c) to more accurately approximate the external location corresponding to the musculoskeletal injury.

9. Method as in claim 8, wherein the step of positioning a marker at an external location adjacent a musculoskeletal injury includes the step of securing the marker at the external location adjacent the musculoskeletal injury.

10. Method as in claim 9, wherein the step of positioning a marker at an external location adjacent the musculoskeletal injury includes positioning an aperture in the marker at the external location adjacent the musculoskeletal injury.

11. Method as in claim 10, wherein the step of simultaneously visualizing the marker and the musculoskeletal injury includes X-raying the marker and the musculoskeletal injury.

12. Method as in claim 11, wherein the step of X-raying includes aiming the X-ray cathode at the aperture, so that the musculoskeletal injury is framed by the marker on the X-ray image.

13. Method as in claim 12, wherein the step of marking an approximate external location corresponding to the musculoskeletal injury includes determining the position of the approximate external location relative to the marker by correlating the position of the musculoskeletal injury relative to the marker on the X-ray.

14. Method as in claim 10, wherein the step of simultaneously visualizing the marker and the musculoskeletal injury includes magnetic resonance imaging of the marker and the musculoskeletal injury.

15. Method as in claim 14, wherein the step of magnetic resonance imaging includes positioning the aperture of the marker and musculoskeletal injury within the magnetic resonance imager so that the musculoskeletal injury is framed by the marker on the magnetic resonance image.

16. Method as in claim 15, wherein the step of marking an approximate external location corresponding to the musculoskeletal injury includes determining the position of the approximate external location relative to the marker by correlating the position of the musculoskeletal injury relative to the marker on the magnetic resonance image.

17. Method as in claim 10, wherein the step of positioning a marker at an external location adjacent a musculoskeletal injury includes placing the marker against a skin location adjacent the musculoskeletal injury.

18. Method as in claim 17, wherein the step of simultaneously visualizing the marker and the musculoskeletal injury includes simultaneously imaging the marker and the musculoskeletal injury with ultrasound.

19. Method as in claim 18, wherein the step of ultrasonic imaging includes positioning an ultrasonic transducer over the skin location adjacent the musculoskeletal injury and the marker, so that the musculoskeletal injury is framed by the aperture in the marker on the ultrasonic image.

20. Method as in claim 19, wherein the step of marking an approximate external location corresponding to the musculoskeletal injury includes determining an approximate skin location of the musculoskeletal injury relative to the marker by correlating the position of the musculoskeletal injury relative to the marker on the ultrasonic image.

21. Method for delivering ultrasonic treatment at a skin location corresponding to a bone injury, comprising the steps of:

a) positioning a marker at an external location adjacent a bone injury;

b) simultaneously visualizing the marker and the bone injury;

c) marking with indicia an approximate external location corresponding to the bone injury; and d) positioning an operative surface of an ultrasonic delivery system adjacent the approximate skin location corresponding to the bone injury.

22. Method as in claim 21, wherein the step of marking an approximate external location corresponding to the bone injury includes the step of marking a medical wrapping of the skin.

23. Method as in claim 22 wherein the step of positioning the operative surface adjacent the approximate skin location corresponding to the internal injury includes the step of removing the medical wrapping at the marking and exposing the skin.

* * * * *